(12) United States Patent
Achim et al.

(10) Patent No.: US 7,041,283 B1
(45) Date of Patent: May 9, 2006

(54) METHODS OF USING IMMUNOPHILIN BINDING DRUGS TO IMPROVE INTEGRATION AND SURVIVAL OF NEURONAL CELL TRANSPLANTS

(75) Inventors: Cristian L. Achim, Allison Park, PA (US); Mihaela Avramut, Pittsburgh, PA (US); Adriana Zeevi, Pittsburgh, PA (US)

(73) Assignee: University of Pittsburgh-Of the Commonwealth System of Higher Education, Pittsburgh, PA (US)

( * ) Notice: Subject to any disclaimer, the term of this patent is extended or adjusted under 35 U.S.C. 154(b) by 308 days.

(21) Appl. No.: 10/073,522

(22) Filed: Feb. 11, 2002

Related U.S. Application Data

(60) Provisional application No. 60/269,583, filed on Feb. 16, 2001.

(51) Int. Cl.
*C12N 12/00* (2006.01)
*A61K 9/00* (2006.01)

(52) U.S. Cl. .................... 424/93.1; 424/93.7; 514/1; 514/2

(58) Field of Classification Search ............... 424/93.1, 424/93.7, 325, 366, 368; 514/1, 2; 435/93.1, 435/93.7, 325, 366, 368
See application file for complete search history.

(56) References Cited

U.S. PATENT DOCUMENTS

| | | | |
|---|---|---|---|
| 5,696,135 A | | 12/1997 | Steiner et al. |
| 5,968,957 A | | 10/1999 | Hamilton et al. |
| 6,080,753 A | | 6/2000 | Lyons et al. |
| 6,121,273 A | | 9/2000 | Hamilton et al. |
| 6,140,116 A | * | 10/2000 | Dinsmore .................. 435/325 |
| 6,258,353 B1 | * | 7/2001 | Isacson et al. ............. 424/93.1 |
| 2002/0110546 A1 | * | 8/2002 | Major et al. ............. 424/93.21 |

OTHER PUBLICATIONS

ADIS R&D Profile (Jan. 1999) "Sirolimus AY 22989, NSC 226080, NSC 606698, Rapamycin, RAPAMUNE" Drugs R&D 1(1100–107.*
Stedman's Medical Dictionary 27th Edition (2000) Lippincott Williams & Wilkins.*
Sigma Aldrich Product Information Cyclosporin A (Product No. C 1832)printed from www.sigma.com on Mar. 23, 2004.*
Sigma Aldrich Product Information Rapamycin (Product No. R 0395) printed from www.sigma.com on Mar. 24, 2004.*
Hale et al. (Feb. 15, 1997) "Superiority of sirolimus (rapamycin) over cyclosporine in augmenting allograft and xenograft survival in mice treated with antilymphocyte serum and donor–specific bone marrow." Transplantation 63(3): 359–64.*

(Continued)

*Primary Examiner*—Elizabeth C. Kemmerer
*Assistant Examiner*—Christopher James Nichols
(74) *Attorney, Agent, or Firm*—Arnold B. Silverman; Eckert Seamans Cherin & Mellott, LLC

(57) ABSTRACT

A method of treatment of neurodegenerative diseases using neuronal cell transplants is provided. The growth, survival and integration of the transplanted neuronal cells is enhanced by a method of culturing the neuronal cells with drugs having an affinity for immunophilins. Immunophilin binding drugs are optionally administered to the patient during transplantation and/or post-operatively. Neurotrophic factors can also be administered to the neuronal cells in vitro, or to the patient during the transplantation procedure and/or post-operatively.

6 Claims, 7 Drawing Sheets

(3 of 7 Drawing Sheet(s) Filed in Color)

OTHER PUBLICATIONS

Fricker–Gates et al. (2001) "Neural Transplantation: Restoring Complex Circuitry in the Striatum." Restorative Neurology and Neuroscience 19(2–3): 119–138.*

Savitz et al. (Jan.–Mar. 2003) "Cell Transplants Offer Promise for Stroke Recovery." The Journal of cardiovascular Nursing 18(1): 57–61.*

Wright et al. (Sep. 1999) "A comparison of the sensitivity of pig and human peripheral blood mononuclear cells to the antiproliferative effects of traditional and newer immunosuppressive agents." Transplant Immunology 7(3): 141–147.*

White et al. (Jan.–Feb. 1999) "Neuron–Enriched Second Trimester Human Cultures: Growth Factor Response and In Vivo Graft Survival." Cell Transplantation 8(1): 59–73.*

Ueda, et al., *Regulation of Endogenous Phosphorylation of Specific Proteins in Synaptic Membrane Fractions from Rat Brain by Adenosine 3':5'–Monophosphate*, The Journal of Biological Chimistry, (Apr. 2, 1973), pp. 8295–8305, 1073, vol. 248, No. 23, Issue of Dec. 10, USA.

Pamnani, et al. *Altered activity of the sodium–potassium pump in arteries of rats with steroid hypertension*, Chemical Science and Molecular Medicine, (1978), pp. 41s–43s, vol. 55.

Steiner et al., *High brain densities of the immunophilin FKBP colocalized with calcineurin*, Nature, (Aug. 13, 1992), pp. 584–587, vol. 358.

Lyons et al., *Immunosuppressant FK506 promotes neurite outgrowth in cultures of PC12 cells and sensory ganglia*, Proc. Natl. Acad. Sci., (Apr. 1994), pp. 3191–3195, vol. 91, USA.

Steiner et al., *Neurotrophic immunophilin ligands stimulate structural and functional recovery in neurodegenerative animal models*, Proc. Natl. Acad. Sci., (Mar. 1997), pp. 2019–2024, vol. 94, USA.

Steiner et al., *Neurotrophic actions of nonimmunosuppressive analogues of immunosuppressive drugs FK506, rapamycin and Cyclosporin A*, Nature Medicine, (Apr. 1997), pp. 421–428, vol. 3, No. 4.

Slader, Jr., et al., *Intrastriatal Grafts from Multiple Donors do not Result in a Proportional Increase in Survival of Dopamine Neurons in Nonhuman Primates*, Cell Transplantation, (1998), pp. 87–96, vol. 7, No. 2.

Costantini, et al., *A Novel Immunophilin Ligand: Distinct Branching Effects on Dopaminergic Neurons in Culture and Neurotrophic Actions after Oral Administration in an Animal Model of Parkinson's Disease*, Neurobiology of Disease, (1998), pp. 97–106, vol. 5, Article No. NB980185.

Sanders, et al., *A murine model of HIV encephalitis: xenotransplantation of HIV–infected human neuroglia into SCID mouse brain*, Neuropathology and Applied Neurobiology, (1998), pp. 461–467, vol. 24.

* cited by examiner

METHODS OF USING IMMUNOPHILIN BINDING DRUGS TO IMPROVE INTEGRATION AND SURVIVAL OF NEURONAL CELL TRANSPLANTS

CROSS REFERENCE TO RELATED APPLICATIONS

This application claims priority under 35 U.S.C. 119(e) to provisional application Ser. No. 60/269,583, filed Feb. 16, 2001. +gi

GOVERNMENT CONTRACT

This invention was made with United States Government support under contract number No. NS33429 awarded by the National Institutes of Health. The Government may have certain rights in this invention.

FIELD OF THE INVENTION

This invention relates to methods of treatment of neurodegenerative diseases using neuronal cell transplants. These transplants have enhanced growth, survival and integration capabilities, and are also the subject of this invention. The growth, survival and integration of the transplanted neuronal cells is enhanced by a method of treating such cells, pre- and post-implantation, with drugs having an affinity for immunophilins.

BACKGROUND INFORMATION

Immunophilins (IP) are receptor proteins having no known cellular function outside their role as receptors for immunosuppressive drugs. Three immunosuppressive drugs that bind to immunophilins are FK506 (Tacrolimus), rapamycin and cyclosporin A, which are used in the treatment of patients after organ transplantation and in selected autoimmune disorders. FK506 and rapamycin are potent immunosuppressive drugs and are activated upon binding to immunophilins designated FK506-binding proteins (FKBPs). Cyclosporin A is of lower potency and higher toxicity than FK506 and rapamycin, and is activated upon binding to cyclophilins. When bound to an immunosuppressive drug, FKBPs and cyclophilins inhibit the activity of calcium-activated phosphatase calcineurin, which leads to inhibition of cytokine synthesis and immunosuppression.

Immunophilins are also known to have peptidyl-prolyl isomerase (PPIase), or rotamase, enzyme activity. Rotamase catalyzes the interconversion of the cis and trans isomers of peptide and protein substrates for the immunophilin proteins. When immunosuppressive drugs or other compounds are bound to the immunophilins, the rotamase activity of the immunophilins is inhibited, an effect unrelated to the immunosuppressive effect of these drugs or compounds. In fact, many compounds have been developed in the laboratory which have an affinity for immunophilins and which inhibit rotamase activity without inhibition of calcineurin and subsequent immunosuppressive effects. Some of these compounds are described, for example, in U.S. Pat. No. 5,696,135 (Steiner et al.).

FK506 has been shown to augment neurite outgrowth in the presence of nerve growth factor (NGF) in PC 12 cells and in rat and chick sensory ganglia explants and has also been shown to increase the number and length of tyrosine hydroxylase-positive neurites in rodent primary dopamine neuronal cultures. In animal models, the drug and its analogues stimulate axonal re-growth and enhance functional recovery following peripheral nerve and spinal cord injury and have protective and regenerative effects in neurotoxic lesions.

FK506 is an immediately available candidate for therapy in treatment of neurodegenerative diseases. It is a small molecule with ready access to the nervous system, and it has been approved for use in humans by the Food and Drug Administration. FK506 is known to act primarily upon lesioned neurons, while sparing the healthy ones. Importantly, FK506 selectively promotes neuronal population growth while inhibiting glial proliferation and can thus specifically target neuronal regeneration and astrocytosis in patients with neural cell transplants. In contrast, traditional neurotrophic peptides have less specific effects. Neurologic adverse effects (including confusion, seizures, tremors, headache) in large part associated with intravenous administration of FK506 have been found to generally subside with oral use or dosage reduction.

Current grafting strategies for neuronal replacement in patients with chronic neurodegenerative diseases include the implantation of first trimester human fetal neuroglial cells with the hope that neuroprogenitor cells will differentiate and survive as functional neurons. Another strategy involves the use of transfected cells grafted in vivo which are proposed to be a stable source of neurotrophic factors (NTF) which promote the survival of residual host neurons. Other treatments include direct delivery in vivo of NTFs, or the use of a NTera-2 teratocarcinoma cell line for grafts, these cells being "neuron-like". None of these strategies deliver the needed long-term clinical improvement.

SUMMARY OF THE INVENTION

The present invention is directed toward methods of treating a neurodegenerative illness with neuronal cell transplants. The methods involve transplanting second trimester or other embryonic or fetal neuronal cells into affected regions of the brain. In addition, the present invention is directed to methods of improving the growth, survival and integration of the transplanted cells using compounds having an affinity for immunophilins. These compounds are administered to human or non-human neuronal cell cultures prior to transplantation and optionally to the patient during and after the transplantation procedure. Diseases appropriate for treatment by the methods of the present invention include Parkinson's disease, ALS, Huntington's disease or other neurodegenerative illnesses.

Second trimester fetal tissue provides a complex cellular environment that supports natural selection of viable neuroglia and contains neuroprogenitor cells that can develop along the neuronal lineage. The neuroglial cells survive and differentiate in vitro as cultures or aggregates, in which they form a complex and abundant network of neuritic processes. These cells can then be transplanted into patients.

It is therefore an aspect of the present invention to provide a method of treating an illness by transplanting neuronal cells which have enhanced growth, survival and integration capabilities into a patient.

It is an additional aspect of the present invention to provide a method of treating an illness by transplanting neuronal cells which have been cultured with compounds having an affinity for immunophilins.

It is an additional aspect of the present invention to provide a method of enhancing the growth, survival and integration capabilities of neuronal cells.

It is a further aspect of the present invention to administer compounds having an affinity for immunophilins to a patient who has received a transplant of neuronal cells.

These and other aspects of the invention will be apparent upon reviewing the attached specification, the figures and appended claims

BRIEF DESCRIPTION OF THE FIGURES

The file of this patent contains at least one color photograph. Copies of this patent with color photographs will be provided by the Patent and Trademark Office upon request and payment of the necessary fee.

FIG. 6C illustrates nestin (green) positive cells expressing neuronal marker MAP-2 (red) after 24 hours in culture. Blue staining is the nuclear stain propidium iodide (Example 3).

FIG. 6E illustrates expression of the neuronal markers MAP-2 (red) and synaptophysin (red) in cells after two weeks in culture (Example 3).

FIG. 6F illustrates cells at four weeks composed of approximately 40% neurons and 40% astrocytes as indicated by staining for class III β-tubulin (green) and GFAP (red). Blue staining is the nuclear stain propidium iodide (Example 3).

DETAILED DESCRIPTION OF THE INVENTION

Figure 1:
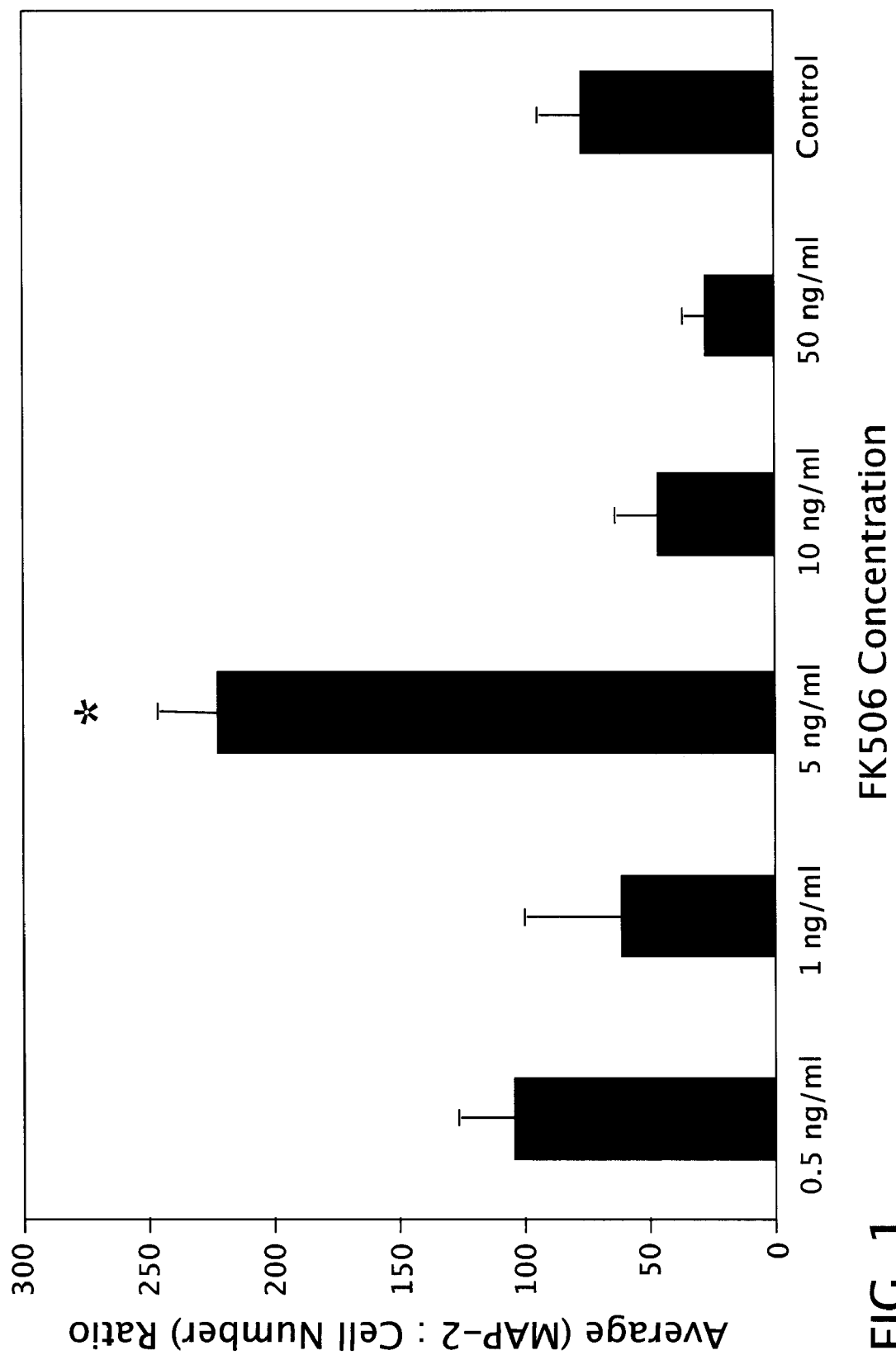
FIG. 1 is a histogram showing neuronal marker MAP-2 expression in human neuroglial cultures following administration of various doses of FK506 (Example 1).

The present invention provides a method for treating a neurodegenerative illness in a patient comprising administering to neuronal cells in vitro at least one compound having an affinity for immunophilins and transplanting the cells into a patient. An effective amount of at least one compound having an affinity for immunophilins is also optionally administered to the patient during the transplantation procedure and post-operatively, after transplantation of the cells. Neurotrophic factors can be administered in combination with the immunophilin binding drugs, both in vitro to the cultured cells or to the patient during the transplantation procedure and/or post-operatively.

"Neurodegenerative illnesses" as used herein includes, but is not limited to, Parkinson's disease, amyotrophic lateral sclerosis (ALS), Alzheimer's disease, Huntington's disease, acute brain degeneration associated with stroke and other neurodegenerative diseases of the central nervous system that are candidates for treatment with tissue grafts of neuronal cells.

"Patient" refers to members of the animal kingdom, including but not limited to humans. Preferably, the methods of the present invention are applied to a patient suffering from any of the illnesses listed above.

As used herein, the term "neuronal cells" refers to any type or source of neuronal cells or neural progenitor cells (such as multipotent neuroepithelial stem cells) appropriate for tissue grafts or transplantation into humans; such cells will be well known to those skilled in the art. Typical types of neuronal cells include, but are not limited to, first or second trimester human embryonic or fetal neuronal cells or neural progenitor cells, porcine fetal or adult brain cells, cell lines such as the Ntera 2/cl. D1 (NT2) human embryonic carcinoma derived cell line (LBS—Neurons), and human cortical neuronal cell line HCN-1. More than one type or source of cells may be used. Preferred are second trimester fetal neuronal cells.

As described above, immunophilins are receptor proteins that bind immunosuppressive drugs and other compounds. Any compound, derivative or fragment thereof having an affinity for immunophilins and which can combine with FKBP or other immunophilins to form a compound-immunophilin complex is contemplated as being within the present invention.

One skilled in the art can determine whether the compound-immunophilin complex is formed by performing an assay to determine the affinity of the compound for immunophilins, such as by the methods taught by Davis, L. D., Soldin, S., *An immunophilin binding assay for sirolimus.* Clinical Therapeutics 22(Suppl. B): B62–B69 (2000); and Goodyear, N, Napoli, KL, Murthy, JN et al., *Radio-receptor assay for sirolimus.* Clin. Biochem. 29: 457–460 (1996). Structures of immunophilin-ligand complexes can be resolved using X-ray crystallography and NMR as described by Ivery, M. *Immunophilins: switched on protein binding domains?* Med. Res. Rev. 20 (6):452:484 (2000); and rotamase activity can monitored using various methods as described by Fischer G., Bang, H., Mech, C., *Detection of enzyme catalysis for cis- trans isomerization of peptide bonds using proline containing peptides as substrates.* Biomed. Biochim. Acta 43:1101–1112 (1984); Lang, K., Schmid, F.X, Fischer, G., *Catalysis of protein folding by prolyl isomerases,* Nature 329:268–270 (1987); and Hsu, V. L., Handschumacher, R.E., Armitage, I. A., *Peptidylprolyl cis-trans isomerase activity of cyclophilin studied by one-dimensional H nuclear magnetic resonance spectroscopy,* J. Am. Chem. Soc. 112:6745–6747 (1990).

Examples of compounds having an affinity for immunophilins include, but are not limited to, FK506, rapamycin, cyclosporin A, FK-520, FK-523, 15-O-DeMe-FK-520, (4R)-[(E)-L-butenyL]-4,N diethyl-L-threonine GPI-1046, V-10,367, and biological equivalents of these compounds. Preferred compounds are FK506, rapamycin and GPI-1046.

As used herein, "biological equivalents" refers to any compound, agent or composition, or combination thereof, which has a similar or identical biological function or effect as the compound to which it is being compared. A biological equivalent of the immunophilin binding drugs includes equivalents to any of the above compounds which can form a complex with any of the immunophilins. One skilled in the art, using the assays noted above, can determine which compounds are biological equivalents to those described herein.

The methods of the present invention are effected through culture of the neuronal cells in vitro with an effective amount of one or more of the immunophilin binding drugs, prior to transplantation of the cells into a patient. The appropriate dosage or "effective amount" of the immunophilin binding drugs and neurotrophic factors, if used, when administered to the cells in culture or to a patient in any given case will vary depending upon certain factors. For cultured cells, an effective amount will depend on factors such as the potency of the drug or neurotrophic factor, the type and number of cells used, and the survival and proliferation of the cells. Generally, the effective amount in vitro will be that amount needed to increase axonal and dendritic growth and synaptogenesis as demonstrated by routine tests used to measure neurite function such as 1) expression of synaptic markers, 2) electron microscopy and 3) electrophysiologic methods such as patch clamping and the like.

Typically, cells will be obtained by methods known to those skilled in the art and cultured using standard tissue culture protocols. The compound or compounds having an affinity for immunophilins will be administered to the cell cultures in nanogram amounts, in the range of about 1–50 ng/ml of culture media. The immunophilin binding compounds are administered to the cell cultures every other day beginning on day 2 for days 2 through 12 in culture, although other regimens are possible and contemplated as being within the scope of the present invention. Cells will be cultured for up to four weeks before implantation; preferred cell types will be isolated using fluorescent activated cell sorting or other sorting methods prior to implantation.

Neurotrophic factors are a group of endogenous, highly homologous proteins that are secreted by cells and are known to regulate the development, maintenance and survival of neurons. As used herein, the term "neurotrophic factor" refers to naturally occurring compounds that are capable of stimulating growth or proliferation of nervous tissue. Neurotrophic factors are generally small, soluble proteins with molecular weights between about 13,000 and 24,000 Daltons.

Many neurotrophic factors are known to those skilled in the art and within the scope of the present invention, and include, but are not limited to, nerve growth factor (NGF), hepatocyte growth factor (HGF), brain-derived neurotrophic factors (BDNF), insulin growth factor (IGF) and its truncated derivatives such as gIGF-1, acidic and basic fibroblast growth factor (aFGF and bFGF, respectively), cytolcines such as platelet-derived growth factors (PDGF), ciliary neurotrophic factors (CNTF), and leukemia inhibitory factor, glial cell line-derived neurotrophic factor (GDNF), neurotrophin-3(NT-3), neurotrophin-4(NT-4) and biological equivalents of these. The preferred neurotrophic factors in methods of the present invention are BDNF and GDNF.

Biological equivalents of neurotrophic factors include equivalents to any of the above compounds, which can elicit the desired neurotrophic effect, and are contemplated as being within the present invention. One skilled in the art can determine the biological equivalence of such compounds by measuring the compound's ability to increase axonal and dendritic growth and synaptogenesis as demonstrated by the routine tests used to measure neurite function described above.

Neurotrophic factors can be used in combination with any of the compounds having an affinity for immunophilins and can be administered to the cells in vitro or to the patient during the transplantation procedure and/or post-operatively. When neurotrophic factors are used in vitro, preferably between about 2–10 ng/ml of culture media is administered to the cultured cells every 48 hours in the culture medium, although other regimens are possible and within the scope of the present invention.

Cells cultured with one or more compounds having an affinity for immunophilins and, optionally the neurotrophic factor or factors, will exhibit enhanced growth, survival and integration capabilities as indicated by increased differentiation of progenitor cells into neuronal cells; increased survival of neuronal cells; increased neurite extension; and expression of synaptic markers. Cells having enhanced growth, survival and integration capabilities are neuronal cells cultured by the above described methods.

Transplantation or tissue grafting procedures known to those skilled in the art can be used to transplant the cultured cells into a patient. Typically, cells will be implanted as an aggregate suspension, with between about $10 \times 10^6$ to about $50 \times 10^6$ cells in each graft. Multiple grafts can also be used. The location of the implant will be in the putarnen, striatum, mesencephalon or other regions of the brain, depending on the neurodegenerative disease being treated. For example, if a patient is being treated for Parkinson's disease, cells will be implanted into the putamen and mesencephalon regions; for Huntington's chorea, implantation will be into the striatum. For stroke victims, the location of implantation will depend on the location and extent of the injury from the stroke.

The methods of the present invention can be further effected through administration to the patient, during transplantation and/or post-operatively, of an effective amount of compounds having an affinity for immunophilins and/or the neurotrophic factors. It will be appreciated that the effective amount in vivo will differ from the effective amount in vitro. The effective amount when administered to a patient will depend on the pharmacodynamic characteristics of the particular compound and its mode and route of administration; the age, general health, metabolism, weight of the patient and other factors which influence response to the compound; the nature and extent of the illness being treated; the kind of concurrent treatment, if any; the frequency of treatment; and the effect desired. Generally, the effective in vivo amount will be that amount of the immunophilin binding drug and/or neurotrophic factor needed to improve long-term functional recovery of the patient as measured by PET imaging, functional MRI evaluation and clinical neurological assessment, without resulting in toxicity to the patient.

If desired, one or more immunophilin binding drugs can be administered to the patient during the transplantation procedure. The one or more immunophilin binding compounds can be solubilized in the cell suspension media in an amount of between about 1–50 ng./ml of suspension media and administered via sterotaxic injection into the graft location along with the cells. Different immunophilin binding drugs can be used in combination during transplantation and post-operatively, and can be the same as or different from the immunophilin binding drugs used in vitro.

Similarly, the neurotrophic factor or factors, if used during transplantation, will also be solubilized in the cell suspension media in an amount of between about 1–50 ng./ml of suspension media and injected into the graft along with the cells.

If administered post-operatively, a daily dosage of about 0.03 mg/kg to 1.0 mg/kg of an immunophilin binding drug can be used, in single or divided doses, with the preferred dose varying according to patient responsivity, sensitivity and the like.

Neurotrophic factors can, optionally, also be administered posttransplantation in a daily dosage of between about 0.03 mg/kg–1.0 mg/kg of the neurotrophic factor.

Administration of the immunophilin binding drugs and neurotrophic factors post-operatively can be accomplished by any conventional means available for use in conjunction with pharmaceuticals, and administration can be either as individual therapeutic agents or in combination with other therapeutic agents known in the art for the illness being treated. The compounds can be administered alone, but are generally administered with a pharmaceutically acceptable carrier selected on the basis of the chosen route of administration and standard pharmaceutical practice. The compositions of the invention may be adapted for oral, parenteral, topical, transdermal, transmucosal, rectal or intranasal administration, and may be in unit dosage form; the term "parenteral" as used herein includes subcutaneous, intravenous, intramuscular, or intrastemal injection or infusion techniques. Methods for preparing the present compositions for use by a patient are well known to those skilled in the pharmaceutical arts; formulations can include one or more fillers or preservatives in addition to the active ingredient and carrier.

"Pharmaceutically acceptable carrier" includes any and all solvents, dispersion media, coatings, isotonic and absorption delaying agents, and the like. The use of such media and agents for pharmaceutically active substances is well known in the art. Use of any of these media or agents is contemplated with the compounds of the present invention, absent compatibility problems with the active compound.

It will be appreciated that the therapeutic benefits of the present invention will be manifest in a variety of ways, depending on the type of cells used or the patient and the illness being treated. More than one therapeutic benefit may be observed. The elicitation of any therapeutic benefit by the present methods is within the scope of the invention. "Treating" and "treatment" refer herein to both therapeutic and prophylactic treatments; for ease of reference, "therapeutic benefit" therefore refers collectively to both therapeutic and prophylactic benefits. Therapeutic benefits that may be achieved according to the present invention include, for example, increasing the number of transplanted neuronal cells surviving in the patient; enhancing host integration of the grafted cells by promoting neurite extension and reducing gliosis; reducing host rejection of the transplanted cells; enhancing axonal re-growth and functional recovery; and enhancing long-term functional recovery of the patient generally as determined by the tests described above.

EXAMPLES

The following examples are intended to illustrate the invention, and should not be construed as limiting the invention in any way.

Example 1

Culture of Cells with Immunophilin Binding Drugs in Vitro

Surgical pathology fetal specimens were collected and processed in accordance with the University of Pittsburgh Human Tissue Committee guidelines. Human telencephalic tissues (18–21 weeks of gestation) were collected and placed in DMEM medium (Life Technologies Inc., Grand Island, N.Y.). The aspiration method of fetal removal did not allow for identification of specific brain structures except the general lobe architecture. Tissue processing followed a modified mouse brain dissociation protocol. Within 1 hour of collection, the brain material was placed in $Ca^{++}$-and $Mg^{++}$-free DPBS (Life Technologies), cleaned of meninges, rinsed and minced. Tissue fragments were incubated in 0.05% trypsin-EDTA with additives (Life Technologies) for 5 min at 37° C. and further dissociated. Trypsin inhibitor (10 mg/ml; Sigma, St. Louis, Mo.) was subsequently added, followed by centrifugation for 5 min at 250×g. After filtering through 70 μm nylon-mesh cell strainers (Becton Dickinson, Franklin Lakes, N.J.), the cell suspension was cleaned by gradient centrifugation through an 8% BSA (Sigma) layer (250×g, 10 min). A second filtering was performed using 70 μm and 40 μm nylon-mesh cell strainers (Becton Dickinson). The single cell suspension was counted on a hemocytometer using trypan blue exclusion, brought to a final density of $10^6$ cells/ml and plated on poly-l-ornithine (Sigma) and laminin (Life Technologies) coated 12 mm glass coverslips (Fisher, Pittsburgh, PA) on 24-well plates (Becton Dickinson).

The inhibitory effect of FK506 on human lymphocyte proliferation was verified, prior to administration of the drug to the second trimester fetal cells, to confirm the potency of the drug used in subsequent experiments.

Throughout the experiments standard tissue culture techniques were used, in combination with the drug protocol. More specifically, cultures were incubated in 10% $CO_2$ at 37° C. and fed every other day for 1, 5, 12, or 21 days with fresh NPMM (Bio Whittaker, San Diego, Calif.), followed by NPMM with or without various concentrations of FK506 (provided by Dr. A. Zeevi) and/or BDNF (5 ng/ml, Promega, Madison, Wis.).

In an attempt to identify the cell phenotype that is most affected by different treatments, the neuroglial cultures were immunostained for the neuronal marker MAP-2 and the astrocytic marker GFAP. After 7 days of treatment, cultures were washed with PBS and PBS with 0.05% Tween 20 (Sigma), fixed with 4% paraformaldehyde for 30 min and then incubated for 30 min with PBS with 0.2% BSA and 0.1% Triton X (Sigma). Without washing, cultures were incubated overnight at 4° C. with the primary antibodies mouse anti-MAP-2(1:500, Stemberger Monoclonals Inc., Baltimore, Md.) and rabbit anti-GFAP (1:100, Dako, Capinteria, Calif.). After thorough washing with PBS+ 0.05% Tween 20, a secondary antibody (FITC-conjugated goat anti- mouse and FITC- conjugated goat anti- rabbit) was applied for 2 hours (1:200, Jackson Immuno, West Grove, Pa.). All antibodies were diluted in common antibody diluent (ScyTek, Logan, Utah). RNase A (10 μg/ml; Sigma) was added during the secondary antibody incubation (20 min), followed by the nuclear stain propidium iodide (5 μg/ml, Sigma). Propidium iodide was used to allow quantification of cell numbers for each treatment condition, using LCM and ImageSpace software as described below. Coverslips were then washed and mounted on glass slides (Fisher) using gelvatol fluorescence mounting medium.

A quantitative assessment of the results (i.e., the numbers of cell nuclei stained with propidium iodide and areas covered by immunofluorescent marker staining) using laser confocal microscopy and ImageSpace software (Molecular Dynamics, Sunnyvale, Calif.) was carried out as follows: six randomly chosen fields were analyzed per coverslip (well). The Argon/Krypton laser confocal microscope 40× objective with oil immersion lens (Model 2001, Molecular Dynamics) was used. Images of 512×512 pixels were collected at a pixel size of 0.5 mm². Vertical sections were acquired in order to define vertical borders for the collection of Z-series. The step size between adjacent sections was 0.50 mm. FITC was excited with a wavelength of 488 nm and collected with a 530DF30 filter. Propidium iodide was excited with a wavelength of 568 nm and collected with a 590DFLP filter. Thresholds were set to eliminate any background signal and maintained throughout the immunofluorescent area quantification process. Positive pixels, converted into $\mu m^2$ of positivity, were tabulated using ImageSpace software over a full Z-series of a given sample. The average number of cells and marker positivity surface over the six fields was considered for statistical analysis, except for the preliminary stage of doseresponse relationship assessment. Significant differences from control were determined using one-tailed Student's t test (layered Bonferroni correction applied).

As described above, FK506 (5 ng/ml) was applied to human neuroglial cultures at days in culture (DIC) 1, 5, 12 and 21. At DIC 1 and 5, after an initial acceleration of neurite sprouting (DIC 2–3) when compared to non-treated samples, the drug-treated cells failed to attach adequately (results not shown). When FK506 was applied every other day, for 7 days, starting at DIC 12, the neurotrophic effects were significant. After 7 days of treatment that started at DIC 12, 5 ng/ml FK506 (6 nM) induced a significant increase in MAP-2 expression when compared to all the other treatments (0.5, 1, 10 and 50 ng/ml) and to untreated cultures (FIG. 1).

Figure 2:
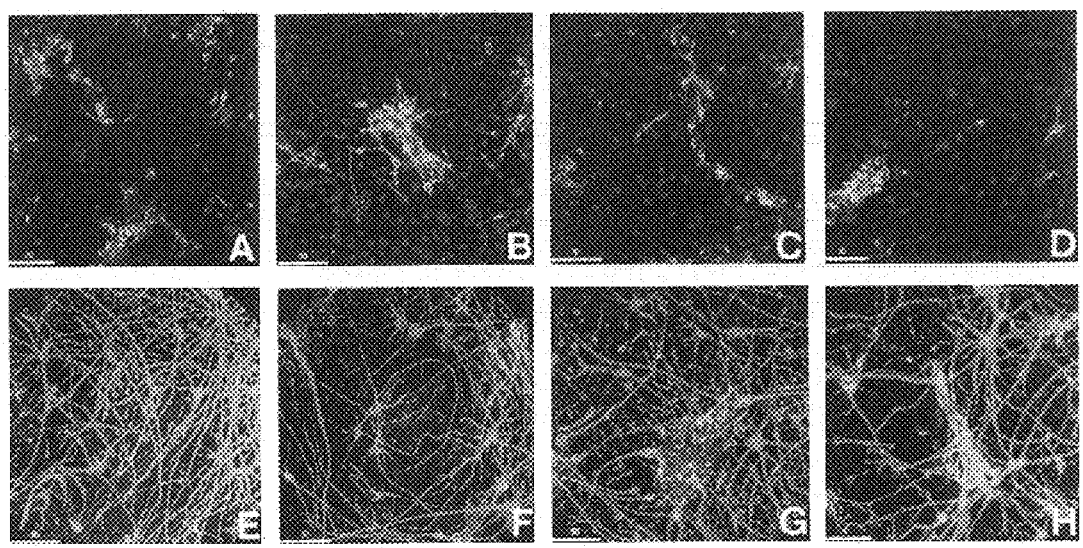
FIGS. 2A–2H contain laser confocal microscopy (LCM) images illustrating the effects of FK506 (B, F); BDNF (C, G); and FK506 combined with BDNF (D, H) in second trimester human neuroglial cells (Example 1). All nuclei are stained with propidiun iodide (red). Frames A–D are images from cells immunostained for neuronal marker MAP-2 (green); frames E–H are images from cells immunostained for astroycytic marker GFAP (green). Frames A and E are untreated controls.

FIG. 2 contains LCM images illustrating the effects of the different treatment regimens. The significant increase in neuronal marker MAP-2 immunostaining (FIG. 2B) and in the MAP-2 surface/cell number ratio (FIG. 4A) suggest that FK506 improves neuronal survival and differentiation in human neuroglial cultures. In contrast, BDNF-induced enhancement of neuronal differentiation was not significant. As shown in FIG. 2B (arrowhead), the neuronal processes stained for MAP-2 were longer and thicker in FK506 treated cultures than in untreated controls (FIG. 2A) and in cultures receiving other treatments (FIGS. 2C and 2D). The size and number of cellular aggregates present in culture were also increased (FIG. 2B, arrow), even in view of the fact that the image analysis system used may have led to an underestimation of the cell numbers (due to the difficulty of discerning cells in close proximity to each other).

Figure 3:
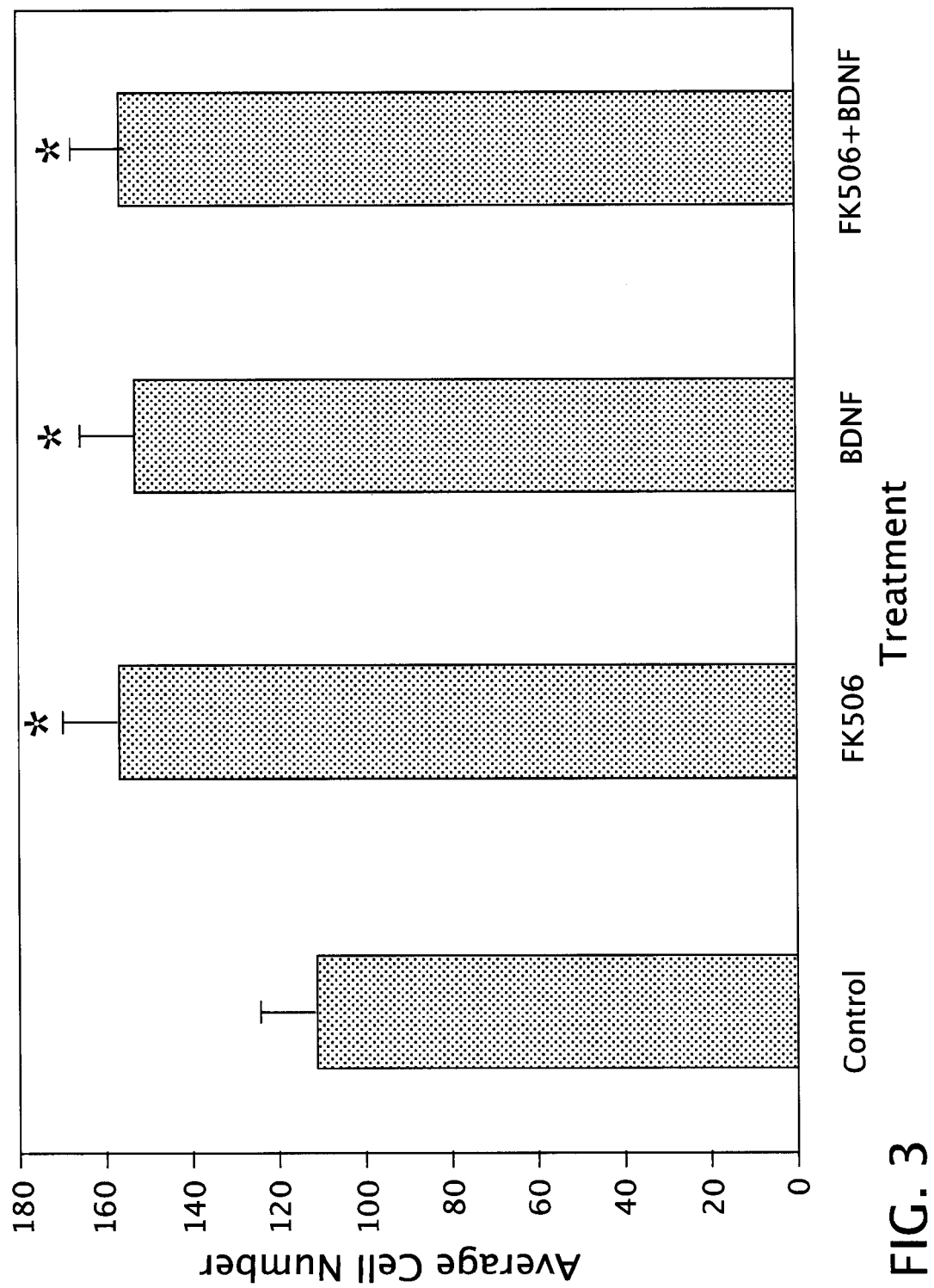
FIG. 3 is a histogram showing average cell numbers in human neuroglial cultures increase following administration of FK506, BDNF or the combination of FK506 and BDNF (Example 1).

A striking increase in cell numbers was seen in cultures treated with FK506 (5 ng/ml) for 7 days, starting at DIC 12(FIG. 3). This increase was comparable to the one induced by BDNF (5 ng/ml). The combination of FK506 (5 ng/ml) and BDNF (5 ng/ml) also induced a marked increase in cell numbers, although it did not produce an additive effect on cell survival and proliferation (FIG. 3). Higher concentrations of FK506 did not appear to exert toxic effects, as the number of cells and MAP-2 surface did not differ significantly from the control.

Figure 4A:
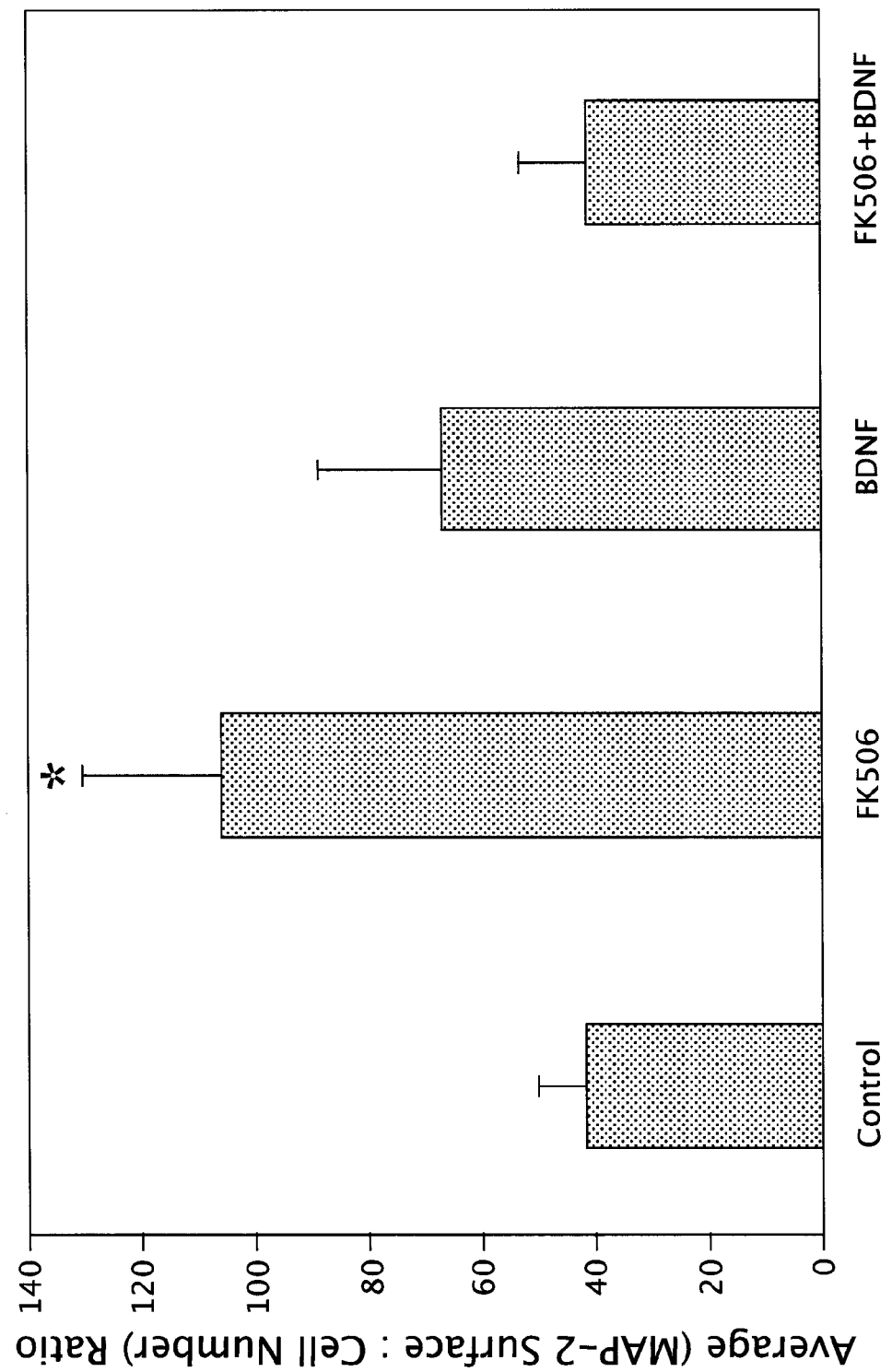
FIG. 4A is a histogram illustrating the effect of FK506, BDNF or combined FK506 and BDNF treatments on MAP-2 expression (Example 1).
Figure 4B:
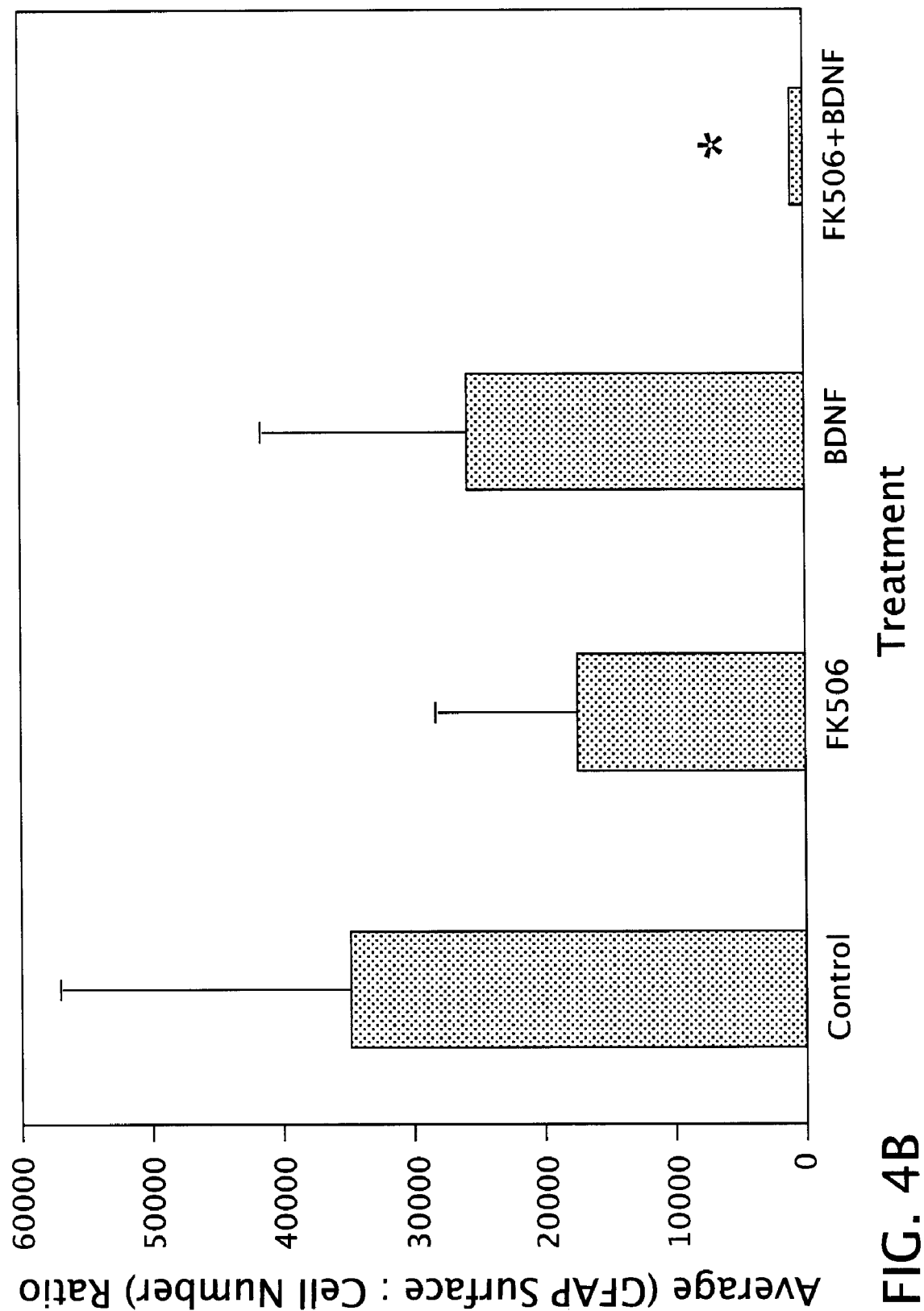
FIG. 4B is a histogram illustrating the effect of FK506, BDNF or combined FK506 and BDNF treatments on GFAP expression (Example 1).

FK506 also exerted an effect on glial cells by reducing their number and/or inhibiting the extension of processes. The absolute area covered by the astrocytic marker GFAP significantly diminished following FK506 treatment (data not shown) and the glial processes appeared slightly sparser and thinner (FIG. 2F) as compared with the untreated control (FIG. 2E); however, the drug-induced decrease in GFAP surface/cell number ratio was not statistically significant (FIG. 4B). GFAP expression decreased after treatment with BDNF alone (FIGS. 2G and 4B) and also markedly decreased after treatment with a combination of FK506 and BDNF (FIG. 2H and FIG. 4B). Indeed, the astrocytic processes in cultures treated with FK506 and BDNF tended to be sparser and thinner (FIG. 2H). The ratio of MAP-2 surface to cell number in BDNF—treated cultures was not significantly different from control (FIG. 4A).

Example 1 indicates that the immunosuppressive macrolide FK506 is neurotrophic in second trimester human fetal neuroglial cultures. The drug potency is remarkable, with only nanomolar amounts increasing cell numbers and neuronal marker MAP-2 expression. FK506 can in fact induce an even stronger increase in neuroglial cells growth than previously assessed. The combination of FK506 and BDNF did not alter the neuronal marker expression.

All three treatments (FK506, BDNF and the combination of FK506 and BDNF) increase the number of cells in culture. FK506 appears to increase the number of neurons and also promote neurite outgrowth. BDNF also tends to increase neurite extension, while modestly increasing neuronal number (NeuN immuno-staining, unpublished observations). When FK506 and BDNF are administered together, however, there is no significant increase in neuronal processes extension.

Example 2

In vivo Grafting of Neuronal Cells.

Second trimester fetal cells grown in suspension at a density of $1 \times 10^6$ cells/mL in 165 cm² vented flasks (Costar, Cambridge, Mass.) formed aggregates within 48 h. After one week in suspension culture, the human neuroglial aggregates (average diameter of 200 □m) were transplanted into the striatum of 4 wk old adult male SCID mice (Tac:Icr:Ha (ICR)-scidfDF-Taconic Laboratories, Gerrnantown, N.Y.). Human neuroglial aggregate suspension was centrifuged for 5 min at 250×g, resuspended in serum-free culture media and transferred to a GASTIGHT 1705 syringe (Hamilton Company, Reno, Nev.). Mice were anesthetized with Metafane inhalant. Stereotaxic unilateral injections of approximately 20 ?l of the dense brain aggregate suspension were made into the striatum. The coordinates of injection were: 2.5 mm lateral to lambda, 5 mm anterior to lambda, and 3.5 mm ventral to the dural surface. Eight mice per group were sacrificed at 2, 4, 8, 16, 24 and 32 wk post-inoculation.

Grafted mice were killed by anesthetic overdose and perfused transcardially with 0.15 M PBS, followed by 4% paraformaldehyde. Brains were postfixed in 4% paraformaldehyde for 24 h and processed for paraffin embedding. Grafts were examined by hematoxylin and eosin staining and immunofluorescent (IF) labeling using antisera to the neuronal markers rabbit anti-human PGP 9.5 (1:400, Accurate Chemical, Westbury, N.Y.), SMI 312 (mouse anti-phosphorylated neurofilaments, 1:1000, Stemberger Monoclonals Inc., Baltimore, Md.), mouse anti-MAP-2 (1:500, Sigma) or rabbit anti-human synaptophysin (1:50, Dako, Capinteria, Calif.); the astrocytic marker rabbit anti-GFAP (1:200, Dako); the human endothelial marker mouse anti-CD31 (1:20, Dako); the human macrophage/microglia marker mouse anti-CD68 (1:100, Dako); and/or the proliferation marker mouse anti-PCNA (1:200, Boehringer Mannheim, Indianapolis, Ind.). Briefly, sections were deparaffinized in Histoclear (National Diagnostics, Atlanta, Ga.), rehydrated and treated with 0.4% pepsin at 37° C. for 8 min. Sections were treated with 5% normal goat serum (Jackson Immuno, West Grove, Pa.) for 30 min and incubated with primary antibody overnight at 4° C. Sections were rinsed in PBS and incubated for 1 hr at room temperature with secondary antibodies conjugated to Texas Red, Cy3, FITC, DTAF or Cy5 (Jackson Immuno). Images were collected by a Laser (Argon/Krypton) Confocal Microscope Model 2001 (Molecular Dynamics) and analyzed using ImageSpace software (Molecular Dynamics) (described in Example 1).

Human CNS grafts recovered at 4, 8 and 16 wk post-transplantation were processed for electron microscopy (EM). Animals were perfused with sodium cacodylate (SC) buffer followed by 4% paraformaldehyde in SC buffer. Brains were removed and grafts were identified under a dissecting microscope. One mm$^3$ blocks were cut and post-fixed in Karnovsky's fixative for 2 hr. Tissues were rinsed in SC buffer three times for 20 min each followed by an overnight rinse at 4° C. and fixation with 1% osmium tetroxide in 5C buffer and 2% uranyl acetate for 60 min. Tissues were then dehydrated in a graded ethanol series and propylene oxide before infiltration with epon-aradite. Resin blocks were cured overnight at 60° C. Silver sections were cut and then stained in 2% uranyl acetate (aqueous) followed by lead citrate. Thin sections were viewed and photographed on a Zeiss EM 10 transmission electron microscope at 60 KV.

Figure 5:
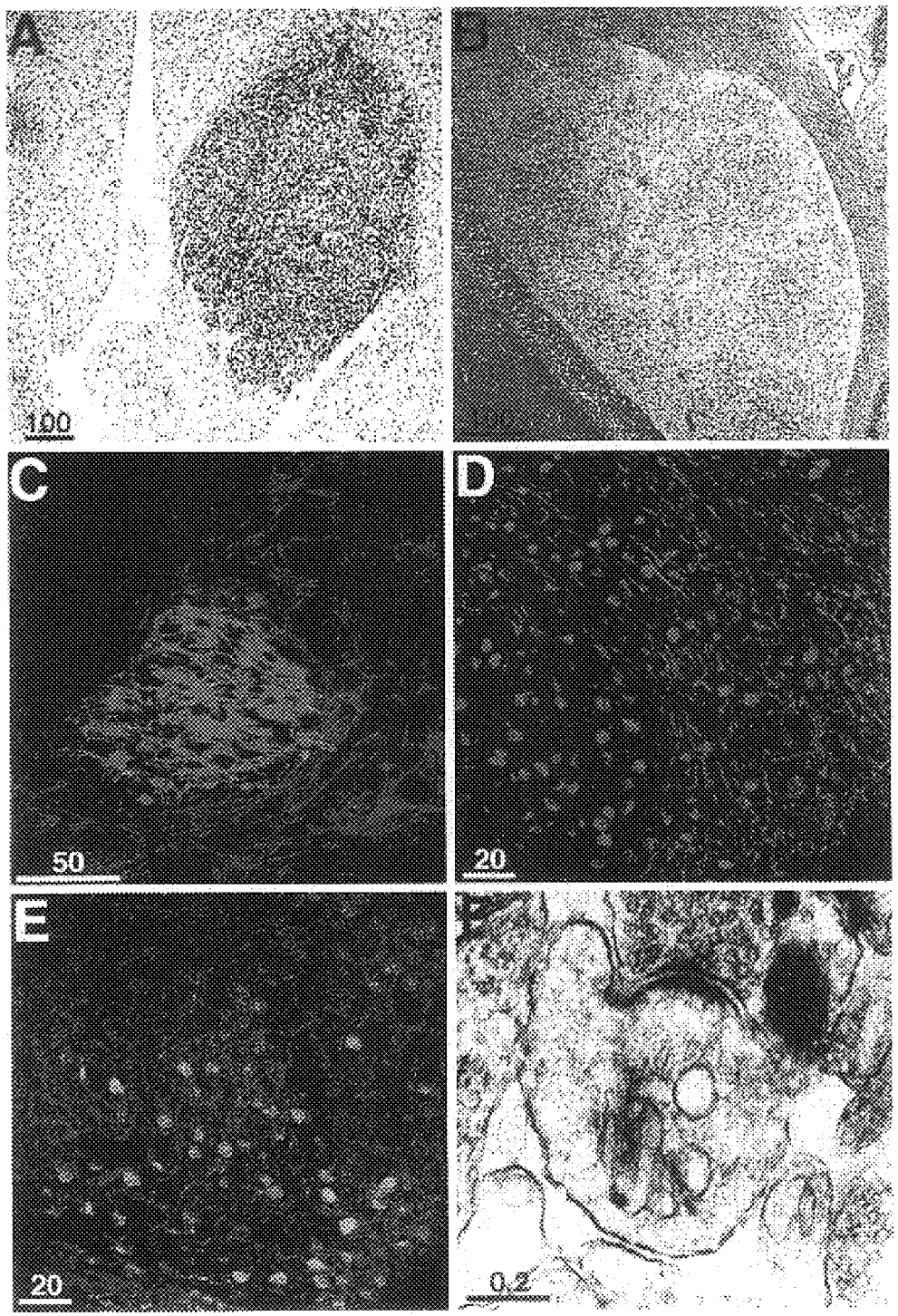
FIG. 5A is a cross-sectional view of a SCID mouse brain one month post-implantation with a human neural graft, stained with hematoxylin and eosin (Example 2).
FIG. 5B is a cross-sectional view of a SCID mouse brain six months post-implantation with a human neural graft, stained with hematoxylin and eosin (Example 2).
FIGS. 5C–E are laser confocal microscopy (LCM) images of grafts immunostained for GFAP, PGP 9.5 and SMI-312 at 21 days, one month and six months post-implantation, respectively (Example 2).
FIG. 5F is an electron microscope image of a graft four months post-implantation (Example 2).

Growth, cellular composition and cytoarchitecture of the grafts were measured for up to 6 months post-implantation. The graft size increased during the first 4 months (FIGS. 5A and 5B). Presence of the proliferative marker PCNA decreased from approximately 10% to 1% within the first 2 months. Intragraft staining for GFAP, approximately 10% of the cells, and ramified microglia, approximately 5%, remained relatively stable over time. Blood vessels, predominantly of murine origin, were seen within the grafts by one month. Host gliosis (FIG. 5C) surrounded the grafts the first month but diminished thereafter. Often, murine macrophage infiltration was evident at early time points (first month). Many grafts were infiltrated again by host macrophages at late time points and had a vacuolated neuropil suggesting degeneration. Grafts decreased in size after four months but remained neuron rich throughout the length of the study (FIGS. 5D and 5E). Occasional synapses, as evidenced by staining for synaptophysin (FIG. 5E) and EM showing synaptic vesicles and pre- and post-synaptic densities (FIG. 5F), were present in the grafts.

Example 2 indicates that primary cultures of second trimester human fetal brain tissues can be successfully grafted into the striatum of SCID mice, survive for at least 8 months, differentiate and form synapses within the graft.

Example 3

Survival of Second Trimester Fetal Cells in Vitro

Figure 6:
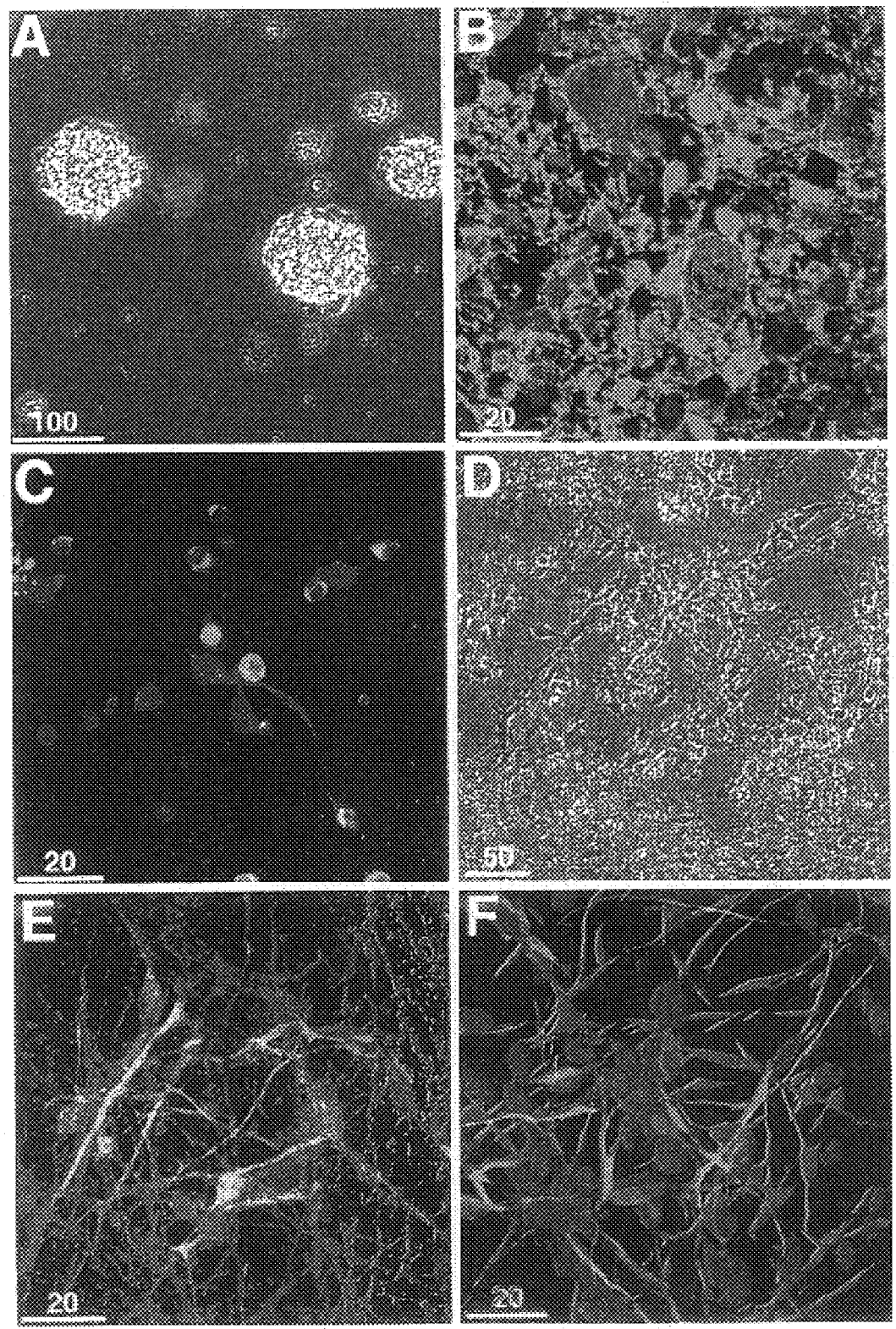
FIGS. 6A and 6D are phase contrast images of second trimester fetal cells grown in suspension at days 4 and 7, respectively (Example 3).
FIG. 6B is an LCM image of second trimester fetal cells grown in suspension and immunostained for RCA-1 (red) and PGP 9.5 (green). Blue staining is the nuclear stain propidium iodide (Example 3).
FIGS. 6C, 6E and 6F are LCM images of second trimester fetal cells cultured on poly-l-ornithine- and laminin-coated surfaces (Example 3).

Single cell suspensions of freshly dissociated second trimester human fetal neuroglia grown at $1 \times 10^6$ cells/nL in serum-free culture media formed spheroid aggregates within 24–48 h (FIG. 6A). By phase-contrast analysis, these aggregates consisted of small, bright cells surrounding a core of one or two larger and darker cells with a morphology consistent with macrophages/microglia By IF analysis, the large cells at the core of the aggregates were confirmed to be of macrophage lineage (e.g. positive for RCA-1) (FIG. 6B). At early time points, within the first two weeks, the aggregates had a diameter between 100 and 200 µm and consisted of approximately 20–30% cells positive for neuronal markers (e.g. PGP 9.5 ), 20% cells positive for astroglial markers (GFAP) and 5% cells positive for microglial markers (e.g. RCA-1).

During the first two weeks in culture, the aggregates continued to grow in size while their cores became more opaque, suggesting possible necrosis associated with poor perfusion. However, a superficial zone of proliferation, occupied by small phase-bright cells, was maintained around the perimeter of the aggregates. Usually during the second week in culture, if left undisturbed, the neuroglial spheroids began forming larger "super-aggregates" that were usually associated with increased central necrosis. Aggregates transferred to coverslips or flasks coated with poly-l-ornithine and laminin attached within hours and was followed by a widespread efflux of cells that was evident by the following day. Cells resembling radial glia extended long processes that seemed to guide the migration of small phase bright cells.

Single cell suspensions of freshly dissociated second trimester fetal brain tissues initially grown in serum-free culture media and poly-l-ornithine and laminin coated tissue culture vessels (flasks or multi-well plates with coated glass coverslips) attached within 24 h. At this time point, numerous cells were positive for the neuroprogenitor cell marker nestin and had already extended neuritic processes (FIG. 6C). By 2 weeks in vitro, the neuritic network had become extensive (FIG. 6D) and its complexity increased for up to 6 months in culture. By double IF LCM, it was evident that neuronal differentiation, measured by the abundance of neuritic processes and synaptic markers (FIG. 6E), continued beyond the first 2 weeks in culture. At the 4 week time point the cellular composition of mixed neuroglial cultures was approximately 40% MAP-2/class III-βtubulin positive, 40% GFAP positive, 5% RCA-1 positive and 15% unlabeled (FIG. 6F). These percentages are representative of cultures derived from various gestational ages and did not vary substantially throughout the time of in vitro growth. Stainings for oligodendroglial markers were negative and endothelial cells (CD31 positive) were only occasionally present. The specificity of the immunostaining with antibodies to the neuroglial precursor marker A2B5 was questionable due to the significant background noise.

Ultrastructural analysis of both aggregate and attached cultures revealed an extensive and healthy neuropil containing abundant neurites filled with microtubules. There was no in vitro evidence of synaptic formation although in many instances neuritic processes in close apposition were found. Example 3 indicates that second trimester fetal neuronal cells survive and differentiate in vitro as attached or aggregate cultures in serum-free media for at least six months.

Whereas particular embodiments of this invention have been described above for purposes of illustration, it will be evident to those skilled in the art that numerous variations of the details of the present invention may be made without departing form the invention as described in the appended claims.

We claim:

1. A method for treating a neurodegenerative illness of the central nervous system in a patient comprising
    culturing human neuronal cells in vitro with an effective amount of at least one immunosuppressive compound having an affinity for immunophilins selected from the group consisting of FK506, cyclosporin A and rapamycin; and transplanting said cultured neuronal cells into said patient, said neurodegenerative illness of the central nervous system selected from the group consisting of Parkinson's disease, Huntington's disease, amyotrophic lateral sclerosis, Alzheimer's disease and stroke, and said effective amount for said cell culturing being between about 1–50 ng/ml.

2. The method of claim 1, further comprising administering to said patient an effective amount of said at least one immunosuppressive compound having an affinity for immunophilins during transplantation of said neuronal cells, said effective amount for said patient being that amount which will promote growth, survival and integration of said neuronal cells.

3. The method of claim 1, wherein said neuronal cells are second trimester human fetal neuronal cells.

4. A method for treating a neurodegenerative illness of the central nervous system in a patient comprising transplanting human neuronal cells, which have been cultured with an effective amount of at least one immunosuppressive compound having an affinity for immunophilins selected from the group consisting of FK506, cyclosporin A and rapamycin into said patient, said neurodegenerative illness selected from the group consisting of Parkinson's disease, Huntington's disease, amyotrophic lateral sclerosis, Alzheimer's disease and stroke, and said effective amount for said cell culturing being between about 1–50 ng/ml.

5. The method of claim 4, further comprising administering to said patient an effective amount of said at least one immunosuppresive compound having an affinity for immunophilins during transplantation of said neuronal cells, said effective amount for said patient being that amount which will promote growth, survival and integration of said neuronal cells.

6. The method of claim 4, wherein said neuronal cells are second trimester human fetal neuronal cells.

\* \* \* \* \*

UNITED STATES PATENT AND TRADEMARK OFFICE
CERTIFICATE OF CORRECTION

| | |
|---|---|
| PATENT NO. | : 7,041,283 B1 |
| APPLICATION NO. | : 10/073522 |
| DATED | : February 11, 2002 |
| INVENTOR(S) | : Cristian L. Achim, Mihaela Avramut and Adriana Zeevi |

It is certified that error appears in the above-identified patent and that said Letters Patent is hereby corrected as shown below:

Column 1, line 10, delete the characters "+gi".

Column 3, line 13, "propidiun" should be change to --propidium--.

Column 4, line 47, "assayfor" should be changed to --assay for--.

Column 4, line 60, "bypro-" should be changed to --by pro- --.

Column 4, line 62, "Peptidylprolyl" should be changed to --Peptidyl prolyl--.

Column 6, line 33, "putarnen" should be changed to --putamen--.

Column 7, line 16, "posttransplantation" should be changed to --post-transplantation--.

Column 7, line 32, "intrastemal" should be changed to --intrasternal--.

Column 8, line 14, "-and" should be changed to --and--.

Column 8, line 53, "Stemberger" should be changed to --Sternberger--.

Column 9, line 22, "doseresponse" should be changed to --dose response--.

Column 9, line 24, the letter "t" after the word "Student's" and before the word "test" should be italized.

Column 9, line 56, insert a space after the "12" in "12(FIG.3)." to correctly read --12 (FIG. 3).--

Column 10, line 47, delete "?" and add the symbol --□--.

Column 10, line 61, "Stemberger" should be change to --Sternberger--

Column 11, line 61, "nL" should be changed to --mL--.

Column 12, line 36, insert a space after the symbol "β" and before the word "tubulin" to correctly read --β tubulin--.

UNITED STATES PATENT AND TRADEMARK OFFICE
CERTIFICATE OF CORRECTION

| | | |
|---|---|---|
| PATENT NO. | : 7,041,283 B1 | Page 2 of 2 |
| APPLICATION NO. | : 10/073522 | |
| DATED | : February 11, 2002 | |
| INVENTOR(S) | : Cristian L. Achim, Mihaela Avramut and Adriana Zeevi | |

It is certified that error appears in the above-identified patent and that said Letters Patent is hereby corrected as shown below:

Column 12, lines 41-42, "endot- helial" should be changed to --endo-thelial--.

Column 12, line 58, "form" should be changed to --from--.

Type here:

Signed and Sealed this

Thirty-first Day of October, 2006

JON W. DUDAS
*Director of the United States Patent and Trademark Office*

UNITED STATES PATENT AND TRADEMARK OFFICE
CERTIFICATE OF CORRECTION

PATENT NO. : 7,041,283 B1
APPLICATION NO. : 10/073522
DATED : May 9, 2006
INVENTOR(S) : Cristian L. Achim, Mihaela Avramut and Adriana Zeevi Page 1 of 2

It is certified that error appears in the above-identified patent and that said Letters Patent is hereby corrected as shown below:

Column 1, line 10, delete the characters "+gi".

Column 3, line 13, "propidiun" should be change to --propidium--.

Column 4, line 47, "assayfor" should be changed to --assay for--.

Column 4, line 60, "bypro-" should be changed to --by pro- --.

Column 4, line 62, "Peptidylprolyl" should be changed to --Peptidyl prolyl--.

Column 6, line 33, "putarnen" should be changed to --putamen--.

Column 7, line 16, "posttransplantation" should be changed to --post-transplantation--.

Column 7, line 32, "intrastemal" should be changed to --intrasternal--.

Column 8, line 14, "-and" should be changed to --and--.

Column 8, line 53, "Stemberger" should be changed to --Sternberger--.

Column 9, line 22, "doseresponse" should be changed to --dose response--.

Column 9, line 24, the letter "t" after the word "Student's" and before the word "test" should be italized.

Column 9, line 56, insert a space after the "12" in "12(FIG.3)." to correctly read --12 (FIG. 3).--

Column 10, line 47, delete "?" and add the symbol --□--.

Column 10, line 61, "Stemberger" should be change to --Sternberger--

Column 11, line 61, "nL" should be changed to --mL--.

Column 12, line 36, insert a space after the symbol "β" and before the word "tubulin" to correctly read --β tubulin--.

UNITED STATES PATENT AND TRADEMARK OFFICE
CERTIFICATE OF CORRECTION

PATENT NO. : 7,041,283 B1
APPLICATION NO. : 10/073522
DATED : May 9, 2006
INVENTOR(S) : Cristian L. Achim, Mihaela Avramut and Adriana Zeevi It is certified that error appears in the above-identified patent and that said Letters Patent is hereby corrected as shown below:

Column 12, lines 41-42, "endot- helial" should be changed to --endo-thelial--.

Column 12, line 58, "form" should be changed to --from--.

Type here:

This certificate supersedes Certificate of Correction issued October 31, 2006.

Signed and Sealed this

Nineteenth Day of December, 2006

JON W. DUDAS
*Director of the United States Patent and Trademark Office*